United States Patent [19]

Ruiz

[11] Patent Number: 5,349,943
[45] Date of Patent: Sep. 27, 1994

[54] MIRROR LARYNGOSCOPE BLADE

[75] Inventor: Ernest Ruiz, Richfield, Minn.

[73] Assignee: Hennepin Faculty Associates, Minneapolis, Minn.

[21] Appl. No.: 110,887

[22] Filed: Aug. 24, 1993

[51] Int. Cl.[5] ............................................. A61B 1/06
[52] U.S. Cl. ........................................ 128/11; 128/10; 128/21
[58] Field of Search ........................ 128/10, 11, 21, 22

[56] References Cited

U.S. PATENT DOCUMENTS

| | | | |
|---|---|---|---|
| 1,945,380 | 1/1934 | Russell | 128/11 |
| 2,014,879 | 9/1935 | Brooks | 128/11 |
| 3,643,654 | 2/1972 | Felbarg | 128/11 |
| 3,870,037 | 3/1975 | Cadariu et al. | 128/10 |
| 3,884,222 | 5/1975 | Moore | 128/11 |
| 3,943,920 | 3/1976 | Kandel | 128/11 |
| 4,827,910 | 5/1989 | Mathews, III | 128/11 |

OTHER PUBLICATIONS

"An Anulgated Laryngoscope for Routine and Difficult Tracheal Intubation", Bellhouse, C.P., *Anesthesiology* Clinical Reports, 69:126–129 (1988).
"Specialized Curved Blades," 1 page from 8-79 Foregger, Puritan–Bennett Catalog.
"A Mirror Laryngoscope," Siker, Anesthesiology, vol. 17, pp. 38–42 (1956).
"Anesthesiology," Siker, JAMA, vol. 243, No. 21, pp. 2179–2180, (1980).

*Primary Examiner*—Richard J. Apley
*Assistant Examiner*—Donna L. Maraglio
*Attorney, Agent, or Firm*—Faegre & Benson

[57] ABSTRACT

A mirror laryngoscope blade includes a curved shaft, a mount on a proximal end of the shaft for attaching the blade to a handle, and a flange extending from an edge of the shaft. The mirror includes a primary viewing surface and a tip inclined toward the shaft. The tip is located between the distal end and the distal quarter-point of the shaft.

21 Claims, 1 Drawing Sheet

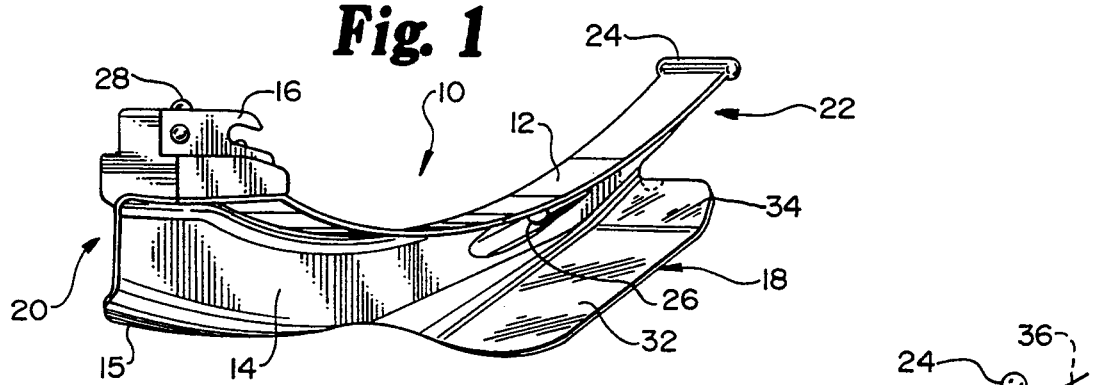
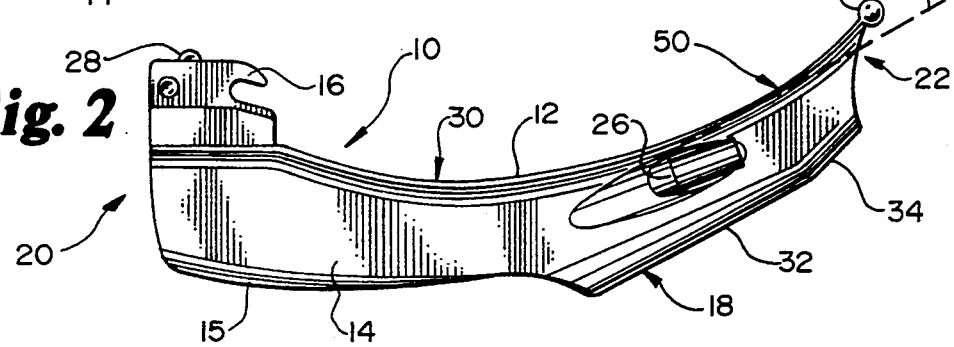
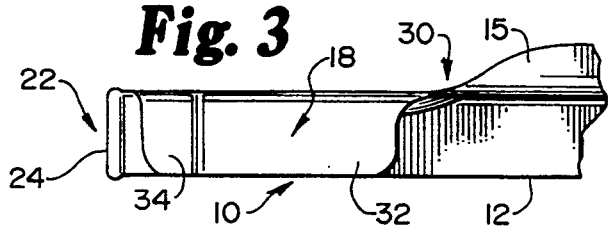
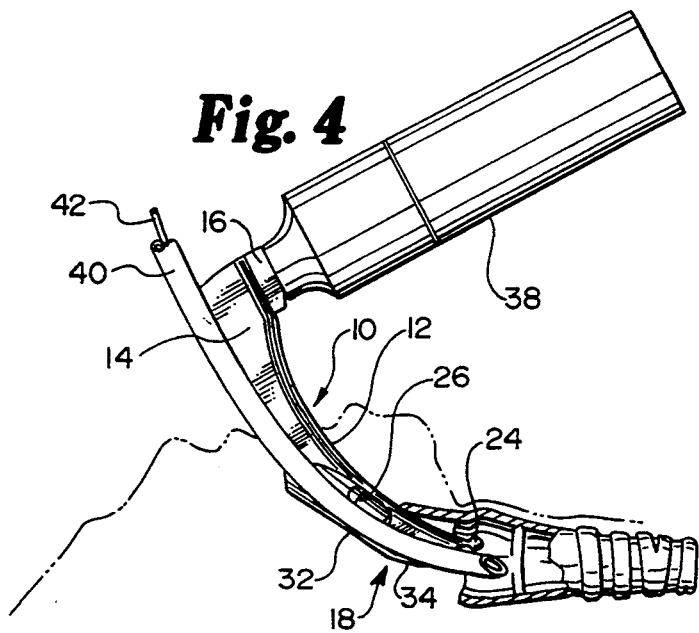

MIRROR LARYNGOSCOPE BLADE

BACKGROUND OF THE INVENTION

The present invention relates generally to laryngoscope blades used to insert tubes into the tracheas of patients during medical procedures. In particular, the present invention is an improved mirror laryngoscope.

Laryngoscopy is a medical procedure in which a laryngoscope blade is inserted into the mouth of a patient to facilitate the physician's visualization of the patient's vocal cords and larynx. This procedure is commonly performed during endotracheal intubation, the insertion of a tube into the trachea of the patient for purposes such as the delivery of oxygen, ventilation, and removal of undesirable objects.

Laryngoscope blades typically include an elongated, generally flat and relatively thin shaft having distal and proximal ends. A small cylindrical member having a diameter greater than the thickness of the shaft extends transversely across the distal end or spatula of the shaft to form a blunt tip. The proximal end of the shaft includes a mount configured to releasably engage a handle. An upper flange extends perpendicularly from one edge of the shaft on the side of the shaft opposite the handle mount. A narrow lower flange extends from the end of the upper flange opposite the shaft, and is generally parallel to the shaft. The shaft and upper and lower flanges are typically fabricated from a single piece of stainless steel or other metal. The handle mount is fabricated as a separate element and welded or otherwise attached to the blade. A lamp is mounted to the upper flange and oriented to direct light toward the distal end of the blade. Electrical leads to the lamp are coupled to contacts on the handle mount through a metal tube. The handle includes a battery pack and electrical contacts that mate with the contacts on the handle mount of the blade.

During laryngoscopy and endotracheal intubation the handle is manipulated to insert the laryngoscope blade into the mouth of the patient. With the help of light provided by the lamp, the physician will visually identify the location of the vocal cords. The distal end of the blade is then used to lift the patient's epiglottis to reveal the cords. A stylet or malleable obturator, an elongated, relatively thin and bendable shaft that retains the shape to which it is bent, is inserted into the endotracheal tube and used to guide the tube past the epiglottis and vocal cords into the patient's trachea. The stylet is then withdrawn from the endotracheal tube and the laryngoscope blade removed from the patient's mouth.

Anatomical variations between patients, such as kyphosis of the cervical spine, an inability to open the mouth or a short mandible, can make laryngoscopy and endotracheal intubation difficult with some patients. There may also be a concern for cervical spine injury, in which case the physician will be reluctant to position the patient's head in the optimal position for laryngoscopy. A variety of different types and sizes of laryngoscopy blades are therefor available to physicians, each especially well suited for use under certain circumstances or with specific anatomical characteristics.

One widely used laryngoscopy blade, commonly known as the Macintosh blade, includes a curved shaft. The curve in the Macintosh blade can, however, make it difficult to visualize the vocal cords during laryngoscopy. To help alleviate this problem, one curved laryngoscope blade, known as the Siker blade, includes a mirror which extends from the upper flange near the midpoint of the shaft. The mirror is polished stainless steel, and can be attached to the flange by a copper jacket to facilitate conduction of the patient's endogenous heat to minimize fogging during use. The Siker blade is inserted into the oral cavity of the patient in the usual manner, with the physician indirectly viewing the vocal cords and other structures at the distal end of the blade by looking into the mirror from the proximal end.

Another mirror laryngoscope blade is disclosed in the Felbarg U.S. Pat. No. 3,643,654. This laryngoscope blade includes two mirrors in the optical path, enabling the physician to see a right-side-up image during laryngoscopy.

Unfortunately, the Siker and Felbarg blades are difficult to use in a variety of circumstances and conditions where the mirror may otherwise be advantageous. For example, these blades can be difficult to place in the mouth of many patients. The blade may also be beyond the vocal cords and into the esophagus before the mirror is even in the patient's mouth. A continuing need therefore exists for mirror laryngoscope blades that can be used on patients having conditions or anatomical characteristics which make laryngoscopy difficult with known blades.

SUMMARY OF THE INVENTION

The present invention is a laryngoscope blade that is especially well suited for laryngoscopy on patients having kyphosis of the spine, short mandibles, mouths that cannot open widely, or possible spinal conditions which prevent the head from being optimally positioned for laryngoscopy. The blade includes an elongated shaft having edges and proximal and distal ends. A mount on the proximal end of the shaft is configured for mounting the blade to a handle. A flange extends from one of the edges of the shaft. A mirror including a primary viewing surface and a tip extends from the flange. The tip is inclined toward the shaft with respect to the primary viewing surface and has at least a portion located between the distal end and distal third-point of the shaft. A physician can relatively easily insert the blade into the mouth of a patient, and use the mirror to visualize the vocal cords. During endotracheal intubation the tip of the mirror can be used to deflect the endotracheal tube, thereby assisting the physician to pass the tube through the vocal cords and into the patient's trachea.

BRIEF DESCRIPTION OF THE DRAWINGS

FIG. 1 is a perspective view of one embodiment of a mirror laryngoscope blade in accordance with the present invention.

FIG. 2 is an actual size side view of the laryngoscope blade shown in FIG. 1.

FIG. 3 is a bottom view of a portion of the laryngoscope blade shown in FIG. 1.

FIG. 4 is an illustration of the laryngoscope blade shown in FIG. 1 mounted to a handle and inserted into the mouth of a patient during laryngoscopy and endotracheal intubation.

DETAILED DESCRIPTION OF THE PREFERRED EMBODIMENTS

A mirror laryngoscope blade 10 in accordance with the present invention is illustrated generally in FIGS. 1-3. Known as the Ruiz blade after its inventor, blade 10 includes a shaft 12, upper flange 14, lower flange 15, mount 16 and mirror 18. Shaft 12 is a curved, elongated and relatively thin member in the embodiment shown, and has a pair of opposite edges. A cylindrical member 24 having a diameter slightly greater than the thickness of shaft 12 is transversely oriented on the shaft at distal end 22 (also known as the spatula) to form a blunt tip. Upper flange 14 is a relatively thin member that extends generally perpendicularly from an edge of shaft 12 on the side of the shaft opposite the mount 16. Lower flange 15 extends from the end of upper flange 14 opposite shaft 12, and is generally parallel to the shaft. In the embodiment shown, the lower flange 15 is relatively narrow, and extends from upper flange 14 only between proximal end 20 and mirror 18. A lamp 26 is mounted to a recess in upper flange 14 and is oriented to direct light toward distal end 22 of blade 10. A tubular metal conduit (not visible in FIGS. 1–3) houses electrical leads coupling lamp 26 to contacts 28 on mount 16. Shaft 12, upper and lower flanges 14 and 15 and mirror 18 can be fabricated from a single piece of stainless steel. Alternatively, mirror 18 can be fabricated as a separate element and welded to upper flange 14. Mount 16 is welded or otherwise fastened to the proximal end 20 of blade 10. Blade 10 can be made in different sizes to accommodate patient's with varying anatomical characteristics.

Mirror 18 is a thin, generally planar, polished stainless steel member that extends from the end of upper flange 14 opposite shaft 12, and from the side of the upper flange opposite lower flange 15. Mirror 18 is therefore positioned below and faces shaft 12. In the embodiment shown, mirror 18 has a width equal to the width of shaft 12. The mirror 18 is located between midpoint 30 and distal end 22 of blade 10 and includes a primary viewing surface 32 and a tip 34. Mirror 18 extends substantially the entire distance between the midpoint 30 and distal end 22 of blade 10 in the embodiment shown. As perhaps best shown in FIG. 2, the primary viewing surface 32 of mirror 18 is oriented generally parallel to a tangent to curved shaft 12 (broken line 36) that intersects the shaft closer to distal end 22 of blade 10 than to midpoint 30. Tip 34 of mirror 18 is inclined upwardly from the primary viewing surface 32, toward shaft 12. Mirror 18 is located with tip 34 within the distal one-quarter or one-third of the length of shaft 12, or within about 5 centimeters of the distal end. In the embodiment shown, tip 34 is located within about three centimeters of distal end 22 of shaft 12, between the distal fifth-point 50 and distal end of the shaft (i.e., within the distal one-fifth of the length of the shaft).

The manner in which laryngoscope blade 10 is used can be described generally with reference to FIG. 4. The patient's oral cavity should be suctioned prior to or during insertion of blade 10 to remove any fluids or material. Mirror 18 should also be coated with anti-fogging solution, or placed in a warm water bath, prior to use to prevent fogging. With a handle 38 that is mounted to blade 10 in a conventional manner, and lamp 26 turned on, distal end 22 of the blade is inserted into the oral cavity. As blade 10 is being inserted, the physician views the structures in the oral cavity at the distal end 22 while looking into mirror 18 from the proximal end 20. Since the mirror 18 is positioned close to distal end 22 of blade 10, and because of the orientation of the mirror with respect to the curve in shaft 12, the physician will be able to visualize the structures in the oral cavity as the blade is being inserted. Once the epiglottis been visualized, the tip of blade 10 is placed under the epiglottis, and the blade lifted to raise the epiglottis anteriorly, allowing the physician to visualize the vocal cords.

Once the vocal cords have been visualized, the physician can proceed with intubation. A malleable obturator 42 is bent to generally conform to the curve in shaft 12 and inserted into endotracheal tube 40. Tube 40 is then guided over mirror 18 toward the vocal cords. Tip 34 of mirror 18 deflects tube 40 and helps the physician guide the tube through the vocal cords and into position. The physician will typically loose sight of the vocal cords during this intubation procedure. Once the endotracheal tube 40 is in place, malleable obturator 42 is removed and any additional procedures performed in a conventional manner.

The mirror laryngoscope blade 10 of the present invention offers considerable advantages over the Siker blade. The blade enables physicians to more clearly visualize the vocal cords in patients having a wide range of conditions and anatomical characteristics. The bent tip of the mirror also assists the physician by guiding the endotracheal tube during the intubation procedure. Mirror laryngoscope blade 10 is therefore a useful. laryngoscopy instrument.

Although the present invention has been described with reference to preferred embodiments, those skilled in the art will recognize that changes may be made in form and detail without departing from the spirit and scope of the invention.

What is claimed is:

1. A laryngoscope blade, including:
    a shaft having edges, and proximal and distal ends;
    a mount on the proximal end of the shaft for mounting the blade to a handle;
    a flange extending from an edge of the shaft; and
    a mirror, including a primary viewing surface and a tip, extending from the flange and facing the shaft, the tip inclined toward the shaft with respect to the primary viewing surface and located between the distal end and distal third-point of the shaft.

2. The laryngoscope blade of claim 1 wherein the mirror has a length extending substantially the entire distance between the midpoint and distal end of the shaft.

3. The laryngoscope blade of claim 1 wherein the mirror is planar.

4. The laryngoscope blade of claim 1 wherein the blade includes a curved shaft.

5. The laryngoscope blade of claim 4 wherein the primary viewing surface of the mirror is parallel with a tangent of the curved shaft closer to the distal end of the shaft than the midpoint of the shaft.

6. The laryngoscope blade of claim 4 wherein the primary viewing surface of the mirror, is parallel with a tangent of shaft adjacent the distal end of the shaft.

7. The laryngoscope blade of claim 1 wherein the shaft, flange and mirror are integral elements formed from one piece of metal.

8. The laryngoscope blade of claim 1 wherein the mirror includes polished reflective metal.

9. The laryngoscope blade of claim 1 wherein the mirror includes polished stainless steel.

10. The laryngoscope blade of claim 1 wherein the shaft, flange and mirror are fabricated from stainless steel or plated metal.

11. The laryngoscope blade of claim 1 and further including a lamp mounted to the flange and facing the distal end of the shaft.

12. The laryngoscope blade of claim 1 wherein the mirror has a width generally equal to a width of the shaft.

13. The laryngoscope blade of claim 1 wherein the tip of the mirror is located between the distal end and distal quarter-point of the shaft.

14. The laryngoscope blade of claim 1 wherein the tip of the mirror is located within about three centimeters of the distal end of the shaft.

15. The laryngoscope blade of claim 1 wherein the tip of the mirror is located within about five centimeters of the distal end of the shaft.

16. A laryngoscope blade, including:
   a curved shaft having edges and proximal and distal ends;
   a mount on the proximal end of the shaft for mounting the blade to a handle;
   a flange extending from an edge of the shaft; and
   a mirror, including a primary viewing surface and a tip, extending from the flange and facing the shaft, the tip inclined toward the shaft with respect to the primary viewing surface and located between the distal end and distal quarter-point of the shaft.

17. The laryngoscope blade of claim 16 wherein the mirror has a length extending substantially the entire distance between the midpoint and distal end of the shaft.

18. The laryngoscope blade of claim 17 wherein the primary viewing surface of the mirror is parallel with a tangent of the curved shaft closer to the distal end of the shaft than to the midpoint of the shaft.

19. The laryngoscope blade of claim 17 wherein the primary viewing surface of the mirror is parallel with a tangent of the curved shaft adjacent to the distal end of the shaft.

20. The laryngoscope blade of claim 16 wherein the shaft, flange and mirror are integral elements formed from one piece of metal.

21. The laryngoscope blade of claim 16 wherein the tip of the mirror is located within about three centimeters of the distal end of the shaft.

* * * * *